United States Patent [19]

Hisano et al.

[11] Patent Number: 4,774,275
[45] Date of Patent: Sep. 27, 1988

[54] POLYPROPYLENE COMPOSITION

[75] Inventors: Shigeo Hisano, Kudamatsu; Yoji Tamano, Shin-Nanyo; Masaji Enokuchi, Tokuyama, all of Japan

[73] Assignee: Tokuyama Soda Kabushiki Kaisha, Yamaguchi, Japan

[21] Appl. No.: 129,964

[22] Filed: Dec. 4, 1987

Related U.S. Application Data

[63] Continuation of Ser. No. 886,174, Jul. 16, 1986, abandoned.

[30] Foreign Application Priority Data

Jul. 17, 1985 [JP]  Japan ................. 60-155949

[51] Int. Cl.$^4$ .......................... C08K 5/06; C08K 5/12; C08K 5/11
[52] U.S. Cl. .................. 524/370; 524/297; 524/314
[58] Field of Search ................. 524/370, 397, 314

[56] References Cited

U.S. PATENT DOCUMENTS

| | | | |
|---|---|---|---|
| 3,030,333 | 4/1962 | Coppinger | 524/370 |
| 3,168,493 | 2/1965 | Coppinger | 524/370 |
| 4,525,469 | 6/1985 | Ueda et al. | 526/138 |
| 4,582,878 | 4/1986 | Chiba et al. | 525/323 |

FOREIGN PATENT DOCUMENTS 1207481 7/1986 Canada .
2043079 10/1979 United Kingdom .

Primary Examiner—Joseph L. Schofer
Assistant Examiner—N. Sarofim
Attorney, Agent, or Firm—Sherman and Shalloway

[57] ABSTRACT

Disclosed is a polypropylene composition comprising (a) 100 parts by weight of a propylene copolymer, (b) 0.01 to 0.5 part by weight of a heat stabilizer and (c) 0.1 to 10 parts by weight of a diphenyl ether compound represented by the following general formula:

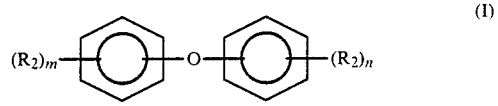

wherein $R_1$ stands for an unsubstituted phenyl group or a phenyl group substituted with an alkyl group having 1 to 4 carbon atoms, or an alkyl group having 10 to 30 carbon atoms, $R_2$ stands for an unsubstituted phenoxy group or a phenoxy group substituted with an alkyl group having 1 to 4 carbon atoms, or an alkyl group having 10 to 30 carbon atoms, and m and n stand for an integer of from 0 to 4, with the proviso that the case where each of m and n is 0 is excluded.

In this polypropylene composition, reduction of the physical properties with the lapse of time after irradiation with radiations, especially bend cracking in the direction parallel to the flow direction of the resin, can be prevented, and discoloration by irradiation with radiations can be controlled. Accordingly, the polypropylene composition of the present invention is suitably used for a medical instrument or a packaging material of a food vessel.

22 Claims, No Drawings

POLYPROPYLENE COMPOSITION

This application is a continuation of application Ser. No. 886,174, filed 7/16/86, now abandoned.

BACKGROUND OF THE INVENTION

1. Field of the Invention

The present invention relates to a polypropylene composition having an improved radiation resistance. More particularly, the present invention relates to a polypropylene composition which does not show substantial reduction of the physical properties or substantial discoloration even long after the composition is irradiated with radiations such as γ-rays or electron beams, and which is suitable as a food packaging material or a medical instrument.

2. Description of the Prior Art

Polypropylene is widely used in various fields and is used especially effectively as a food packaging material and film and recently as a medical instrument such as a syringe. Generally, various stabilizers are incorporated into polypropylene so as to impart a good stability at the molding step and a good practical durability to a molded article. When a vessel or film having a food or farm product packaged therein or a medical instrument is used, an irradiation treatment with radiations such as γ-rays or electron beams is generally carried out so as to attain a sterilizing or insecticidal effect on the vessel, film or medical instrument inclusive of the content or to prevent germination of the content. However, a polypropylene composition having a stabilizer incorporated therein is defective in that after irradiation with radiations, the mechanical strength is reduced or discoloration is caused. If this polypropylene is irradiated with γ-rays at a dose of 2.5 Mrad which is ordinarily regarded as a safe and effective dose for sterilization of medical instruments, reduction of the mechanical strength, which is due to decomposition and deterioration of polypropylene, is conspicuous.

As means for solving the problem of the radiation resistance, there have been proposed a method in which a phenolic antioxidant having an isocyanurate group and a thio co-reagent are incorporated in polypropylene (Japanese Patent Application Laid-Open Specification No. 137135/80), a method in which a triaryl phosphite type antioxidant is incorporated in polypropylene (Japanese Patent Application Laid-Open Specification No. 179234/82), a method in which a heterocyclic hindered amine compound and 1,3,5-tris(3-hydroxy-2,6-dimethyl-4-alkylbenzyl)isocyanurate are incorporated into polypropylene (Japanese Patent Application Laid-Open Specification No. 42638/83) and a method in which a plasticizing additive such as liquid paraffin or a phthalic acid ester oil and a heterocyclic hindered amine are incorporated into polypropylene (Japanese Patent Application Laid-Open Specification No. 201849/83).

In the polypropylene compositions obtained according to these methods, the physical properties are improved to some extent over those of the conventional polypropylene compositions. However, when these improved polypropylene compositions are used in the above-mentioned application fields, they are still insufficient in the processability and physical properties.

SUMMARY OF THE INVENTION

It is therefore a primary object of the present invention to provide a polypropylene composition excellent in the processability.

Another object of the present invention is to provide a polypropylene composition excellent in the radiation resistance.

Still another object of the present invention is to provide a polypropylene composition which is characterized in that even after a molded article of the composition is irradiated with γ-rays or electron beams, discoloration is not caused and reduction of the mechanical strength is controlled.

In accordance with the present invention, there is provided a polypropylene composition comprising (a) 100 parts by weight of a propylene copolymer, (b) 0.01 to 0.5 part by weight of a heat stabilizer and (c) 0.1 to 10 parts by weight of a diphenyl ether compound represented by the following general formula:

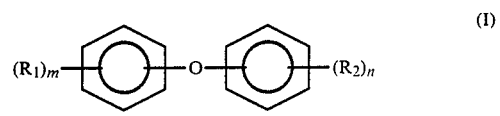

(I)

wherein $R_1$ stands for an unsubstituted phenyl group or a phenyl group substituted with an alkyl group having 1 to 4 carbon atoms, or an alkyl group having 10 to 30 carbon atoms, $R_2$ stands for an unsubstituted phenoxy group or a phenoxy group substituted with an alkyl group having 1 to 4 carbon atoms, or an alkyl group having 10 to 30 carbon atoms, and m and n stand for an integer of from 0 to 4, with the proviso that the case where both m and n is 0 is excluded.

In accordance with a preferred embodiment of the present invention, there is provided a polypropylene composition comprising the above-mentioned components (a), (b) and (c), and (d) 0.5 to 10 parts by weight of an ester of an aromatic dibasic acid having 8 to 12 carbon atoms or an aliphatic dibasic acid having 4 to 10 carbon atoms with an alkyl group having 1 to 18 carbon atoms.

Other objects and features of the present invention will become apparent from the following detailed description.

DETAILED DESCRIPTION OF THE PREFERRED EMBODIMENTS

The first component (a) of the polypropylene composition of the present invention is a propylene copolymer. Various propylene copolymers are widely used as molding materials in various fields, and in the present invention, these known propylene copolymers can be used without any limitation. A random or block copolymer of propylene with 0.5 to 5% by weight, especially 1 to 4% by weight, of other copolymerizable olefin such as ethylene or butene is preferably used as the propylene copolymer.

In the polypropylene composition of the present invention, the propylene copolymer can be blended with up to 20% by weight of other polymer. As other polymer to be blended, there can be mentioned homopolypropylene, high-density polyethylene, low-density polyethylene, polyvinyl acetate, an ethylene/vinyl acetate copolymer, an ethylene/butene copolymer, poly-2- methylpentene-1, a styrene/butadiene/styrene copolymer, a styrene/ethylene/butadiene/styrene copolymer and a mixture of a styrene/ethylene/butadiene copolymer and a polysiloxane.

The second component (b) of the polypropylene composition of the present invention is a heat stabilizer. When a thermoplastic resin is molded or a molded article is treated under elevated temperature, a heat stabilizer is ordinarily added to the thermoplastic resin during or before the molding operation. The heat stabilizer is called "thermal stabilizer", "antioxidant", "radical chain inhibitor" or "peroxide decomposing agent" according to the intended use. In the present invention, known heat stabilizers can be used without any limitation. For example, there are preferably used radical chain inhibitors such as mono-, bis- and tris-phenols and aromatic amines, and peroxide decomposing agents such as mercaptans, mono-, di- and polysulfides, dithiocarbamates, phosphites, phenothiazines and dialkyl esters of thio-di-fatty acids. Among these stabilizers, a triaryl phosphite type stabilizer, a pentaerythritol phosphite type stabilizer, an isocyanurate group-containing phenolic stabilizer, a hindered amine type stabilizer and a mixture thereof are especially preferred.

As specific examples, there can be mentioned triaryl phosphite type stabilizers such as tris(2,4-di-tert-butylphenyl)phosphite, pentearythritol phosphite stabilizers such as distearylpentaerythritol diphosphite, isocyanurate group-containing phenolic stabilizers such as tris(3,5-di-tert-butyl-4-hydroxyphenyl)isocyanurate, 1,3,5-tris(4-tert-butyl-3-hydroxy-2,6-dimethylbenzyl)isocyanurate and 1,3,5-tris(β-(3,5-di-tert-butyl-4-hydroxyphenyl)propionyloxyethyl)isocyanurate, and hindered amine stabilizers such as dimethyl succinate-1-(2-hydroxyethyl)-4-hydroxy-2,2,6,6-tetramethylpiperazine polycondensate, 4-benzoyloxy-2,2,6,6-tetramethylpiperidine, poly(6-(1,1,3,3-tetramethylbutyl)imino-1,3,5-triazin-2,4-diyl)((2,2,6,6-tetramethyl-4-piperidyl)imino)hexamethylene((2,2,6,6-tetramethyl-4-piperidyl)imino), bis(2,2,6,6-tetramethyl-4-methylpiperidine)-sebacate, di-(1,2,2,6,6-pentamethyl-4-piperidyl)-2-n-butyl-2-(3,5-di-tert-butyl-4-hydroxybenzyl)malonate and bis(2,2,6,6-tetramethyl-4-carbonyloxypiperidino)-p-dimethylbenzyl. A hindered amine type stabilizer such as bis(2,2,6,6-tetramethyl-4-piperidine)sebacate or a polymer type hindered amine is especially preferred.

The third component (c) of the polypropylene composition is a diphenyl ether compound represented by the following general formula (I):

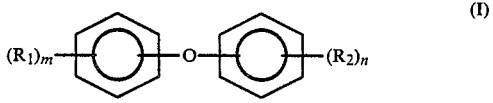

wherein $R_1$ stands for an unsubstituted phenyl group or a phenyl group substituted with an alkyl group having 1 to 4 carbon atoms, or an alkyl group having 10 to 30 carbon atoms, $R_2$ stands for an unsubstituted phenoxy group or a phenoxy group substituted with an alkyl group having 1 to 4 carbon atoms, or an alkyl group having 10 to 30 carbon atoms, and m and n stand for an integer of from 0 to 4, with the proviso that the case where each of m and n is 0 is excluded.

Diphenyl ether compounds represented by the general formula (I) are known as radiation-resistant lubricating oils. In the present invention, these known compounds can be used without any limitation. As preferred examples, there can be mentioned compounds represented by the following formulae:

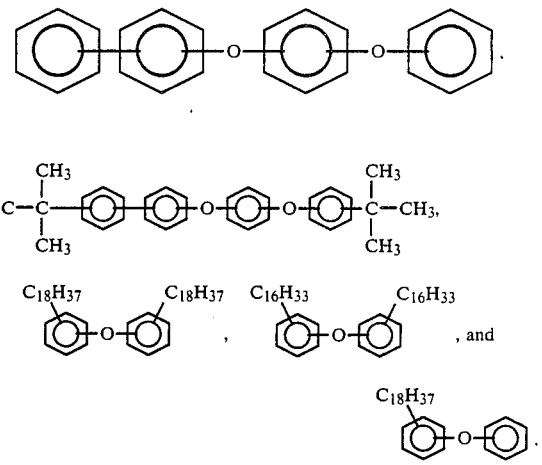

Incidentally, a compound of the general formula (I) in which each of m and n is 0, that is, diphenyl ether, cannot be used because the processability characteristics cannot be improved.

The polypropylene composition of the present invention comprises 100 parts by weight of the first component (a), 0.01 to 0.5 part by weight of the second component (b) and 0.1 to 10 parts by weight of the third comonent (c).

As pointed out above, the second component (b) is incorporated in an amount of 0.01 to 0.5 part by weight, preferably 0.05 to 0.3 part by weight, per 100 parts by weight of the propylene copolymer as the first component (a). If the amount of the component (b) is smaller than 0.01 part by weight per 100 parts by weight of the component (a), the thermal stability at the molding step is reduced. In case the amount of the component (b) is larger than 0.5 parts by weight per 100 parts by weight of the component (a), the processability at the molding step is reduced and bleed-out of the stabilizer from the molded article is caused. In the present invention, if 0.01 to 0.5 part by weight of the stabilizer per 100 parts by weight of the propylene copolymer comprises 0.03 to 0.2 part by weight of a triaryl phosphite type stabilizer or a pentaerythritol phosphite type stabilizer, 0.01 to 0.2 part by weight of an isocyanurate group-containing phenolic stabilizer and 0.05 to 0.5 part by weight of a hindered amine type stabilizer, reduction of the physical properties and discoloration after irradiation with radiations can be further controlled.

In the polypropylene composition of the present invention, the diphenyl ether compound as the third component (c) is incorporated in an amount of 0.1 to 10 parts by weight, preferably 0.2 to 5 parts by weight, per 100 parts by weight of the propylene copolymer as the component (a). If the amount of the component (c) is smaller than 0.1 part by weight per 100 parts by weight of the component (a), the effect of controlling reduction of the physical properties after irradiation with radiations is insufficient, and if the amount of the component (c) is too large, the practical hardness is insufficient or a problem of the surface tackiness arises.

In the polypropylene composition of the present invention, by incorporating the above-mentioned components (a), (b) and (c) in specific amounts, these components exert a synergistic action, and even after the polypropylene composition and a molded article prepared therefrom are irrdiated with radiations, the physical properties are not substantially reduced. Especially usually observed sharp reduction of flexural strength in the direction parallel to the flow direction of the material of molded article from polypropylene, which was heat treated after irradiation with radiations is remarkably controlled. Accordingly, excellent effects can be attained according to the present invention.

Though some excellent effects can be attained by the polypropylene composition of the present invention, according to the kinds of the components (a), (b) and (c) and the amounts thereof, it sometimes happens that the molded article is somewhat discolored by irradiation with radiations. In this case, a dibasic acid ester as the component (d) is incorporated in addition to the foregoing components (a), (b) and (c), whereby the discoloration is effectively prevented. Moreover, the dibasic acid ester as the component (d) exerts an effect of reducing the amounts incorporated of the components (b) and (c). Namely, especially good results can often be obtained by incorporation of the dibasic acid ester component (d).

The dibasic acid ester which is the fourth component (d) of the polypropylene composition of the present invention is an ester of an aromatic dibasic acid having 8 to 12 carbon atoms or an aliphatic dibasic acid having 4 to 10 carbon atoms with an alkyl group having 1 to 18 carbon atoms, preferably 4 to 10 carbon atoms. Known allyl esters of dibasic acids can be used in the present invention without any limitation. As preferred examples, there can be mentioned alkyl adipates, alkyl azelates, alkyl sebacates, alkyl phthalates and alkyl naphthalene-dicarboxylates. The alyl group is an alkyl group having 1 to 18 carbon atoms, preferably 4 to 10 carbon atoms. For example, there can be mentioned a methyl group, an ethyl group, a butyl group, a hexyl group, an octyl group, an ethylhexyl group, an isononyl group, a decyl group and an octyldecyl group. As especially preferred examples, there can be mentioned dialkyl phthalates such as dibutyl phthalate, diheptyl phthalate, diethylhexyl phthalate, diisononyl phthalate, dioctyl phthalate and dioctyldecyl phthalate, dialkyl adipates such as dibutyl adipate, di-n-hexyl adipate and diethylhexyl adipate, dialkyl azelates such as dibutyl azelate and diethylhexyl azelate, and dialkyl sebacates such as dibutyl sebacate and diethylhexyl sebacate.

The alkyl ester of the dibasic acid is incorporated in an amount of 0.5 to 10 parts by weight, preferably 1 to 5 parts by weight, per 100 parts by weight of the propylene copolymer as the component (a).

Customary methods can be adopted for incorporating the above-mentioned components (b) through (d) into the propylene copolymer. Generally, there is preferably adopted a method in which the stabilizer (b) is incorporated into the propylene copolymer, the mixture is preliminarily blended and the mixture is kneaded with the component (c) or the components (c) and (d) by an extruder. Incidentally, in addition to the foregoing components (b) through (d), known additives such as neutralizing agents (dispersants), lubricants, clarifiers, nucleating agents and antistatic agents can be incorporated so far as attainment of the intended effects is not inhibited. A stearic acid salt (calcium stearate) is ordinarily added as a thermal stabilizer.

In the polypropylene composition of the present invention, reduction of the physical properties with the lapse of time after irradiation with radiations, especially sharp reduction of flexural strength in the direction parallel to the flow direction of the resin, can be prevented, and discoloration by irradiation with radiations can be controlled. Accordingly, the polypropylene composition of the present invention is suitably used for a medical instrument or a packaging material of food.

The present invention will now be described in detail with reference to the following example that by no means limits the scope of the invention.

Abbreviations of the additives used in the example are as follows.

A: m-(m-phenoxyphenoxy)diphenyl

B: mixture comprising 50% by weight of monoalkyl diphenyl ether $B_1$ (the alkyl group having 18 carbon atoms) and 50% by weight of dialkyl diphenyl ether $B_2$ (the alkyl group having 16 carbon atoms)

$D_1$: dioctyl phthalate $E_1$: dibutyl sebacate $E_2$: dioctyl adipate $F_1$: distearylpentaerythritol diphosphite $F_2$: tris(2,4-di-tert-butylphenyl)phosphite $G_1$: tris(3,5-di-tert-butyl-4-hydroxyphenyl)isocyanurate $G_2$: 1,3,5-tris(4-tert-butyl-3-hydroxy-2,6-dimethylbenzyl)isocyanurate $G_3$: tris($\beta$-(3,5-di-tert-butyl-4-hydroxyphenyl)propionyloxyethyl)isocyanurate $I_1$: 1,3,5-trimethyl-2,4,6-tris(3,5-di-tert-butyl-4-hydroxybenzyl)benzene $I_2$: n-octadecyl-3-(4'-hydroxy-3',5'-di-tert-butylphenol)propionate $I_3$: 2,6-di-tert-butyl-4-methylphenol $H_1$: dimethyl succinate-1-(2-hydroxyethyl)-4-hydroxy-2,2,6,6-tetramethylpiperidine polycondensate (having a molecular weight of at least 3000)

$H_2$: poly{(6-(1,1,3,3-tetramethylbutyl)imino-1,3,5-triazin-2,4-diyl)((2,2,6,6-tetramethyl-4-piperidine)imino)hexamethylene((2,2,6,6-tetramethyl-4-piperidyl)imino)} (having a molecular weight of at least 2500)

$H_3$: bis(2,2,6,6-tetramethyl-4-piperidyl)sebacate

EXAMPLE (1) Incorporation of Respective Components into Polymer

Components shown in Table 1 in amounts shown in Table 1 and 0.15 part by weight of calcium stearate incorporated into 100 parts by weight of a polymer shown below and having a melt flow rate shown below (g/min; as measured at 230° C. according to ASTM D-1238), and the mixture was preliminarily blended by a Henschel mixer.

(a) An ethylene/propylene random copolymer having an ethylene content of 1.5% by weight and a melt flow rate of 20 (runs 1 through 23).

(b) An ethylene/propylene block copolymer having an ethylene content of 2.5% by weight and a melt flow rate of 20 (runs 24 and 25).

(c) A propylene homopolymer having a melt flow rate of 20 (runs 26 and 27).

(2) Pelletization

The mixture obtained in (1) above was pelletized by a vent extruded having 65 mm diameter screw at resin temperature of 230° C. (supplied by Kobe Seikosho).

(3) Preparation of Test Pieces

The following test pieces were prepared by molding the pellet obtained in (2) above at a molding temperature of 250° C. by using an 8-oz injection molding machine (supplied by Nippon Seikosho).

(i) Sheet having a thickness of 1 mm (50 mm×80 mm).

(ii) Syringe having an inner volume of 10 ml and comprising a barrel portion having an inner diameter of 16.0 mm and a thickness of 1.0 mm and a tip portion (needle-attaching portion) having a thickness of 1.0 mm and a length of 10.0 mm.

(4) Irradiation with Radiations and Heat Treatment

Each of the test pieces (i) and (ii) obtained in (3) above was irradiated with γ-rays at a dose of 5.0 Mrad at a rate of 2 Mrad/hr by using a cobalt 60 irradiator (supplied by Canadian Atomic Energy Bureau).

The irradiated test pieces were allowed to stand still at 60° C. for 30 days in a trust oven (supplied by Toyo Kagaku) while circulating air at an air substitution rate of 1 volume/min. Then, the test pieces were allowed to stand still at 23° C. for 2 days.

(5) Tests

The test pieces obtained in (4) above were subjected to the following tests. The obtained results are shown in Table 1.

(A) Yellowing Test

The sheet (i) mentioned above was used for the test, and the yellowness index (YI) was measured according to ASTM D-1925 on the irradiated sample (sample 1) and the sample allowed to stand still at 60° C. for 30 days after the irradiation (sample 2). In Table 1, the yellowness index (YI) after the irradiation and the yellowness index change ($\Delta YI=$(YI of sample 2)—(YI of sample 1)) are shown in Table 1.

(B) Bend Cracking Test

The sheet (i) was used as the test piece and the autograph bend cracking test was carried out according to ASTM D-790. More specifically, the central portion of the test piece was set at a crosshead in parallel to the flow direction of the resin, and the bend cracking test was carried out in parallel to the orientation direction at a dropping speed of 300 mm/min. The maximum down stroke (bending depth) was 6 mm, and it was checked whether or not the test piece is cracked at a down stroke of up to 6 mm. With respect to each sample, three test pieces were tested, and the average value was calculated. It was checked whether or not the test piece was cracked, and in the case where the test piece was cracked, the down stroke at which the test piece was cracked is shown by the parenthesized value in Table 1.

(C) Falling Weight Break Test

The syringe (ii) was used as the test piece. A hitting metal fitting was attached to the top of the tip portion of the syringe, and a weight of 300 g was dropped from a certain height and it was checked whether or not the syringe was broken. The minimum height at which the shringe was broken is shown in Table 1.

TABLE 1

| Run No. | Stabilizer (parts by weight) | | | | | | | | | Diphenyl Ether Compound (parts by weight) | | |
|---|---|---|---|---|---|---|---|---|---|---|---|---|
| | Phosphite Type | | Isocyanurate Phenol Type | | Hindered Amine Type | | Other Phenol Type | | | A | B | A + B$_2$** |
| 1 | | | | | | | I$_1$ | 0.1 | | 2.0 | | |
| 2 | | | | | | | I$_2$ | 0.1 | | | 2.0 | |
| 3 | | | | | | | I$_3$ | 0.1 | | | | 2.0 |
| 4 | F$_1$ | 0.05 | | | | | | | | | 2.0 | |
| 5 | F$_1$ | 0.05 | G$_1$ | 0.03 | | | | | | | 2.0 | |
| 6 | F$_1$ | 0.05 | G$_1$ | 0.03 | H$_1$ | 0.10 | | | | | 2.0 | |
| 7 | | | | | H$_1$ | 0.10 | | | | | 2.0 | |
| 8 | | | G$_1$ | 0.03 | H$_1$ | 0.10 | | | | | 2.0 | |
| 9 | F$_2$ | 0.05 | | | | | | | | | 2.0 | |
| 10 | | | | | | | I$_1$ | 0.1 | | | 2.0 | |
| 11 | F$_1$ | 0.05 | G$_1$ | 0.03 | H$_1$ | 0.10 | | | | | 0.3 | |
| 12 | F$_1$ | 0.05 | G$_1$ | 0.03 | H$_1$ | 0.10 | | | | | 0.3 | |
| 13 | F$_1$ | 0.05 | G$_1$ | 0.03 | H$_1$ | 0.10 | | | | | 0.3 | |
| 14 | F$_1$ | 0.05 | G$_1$ | 0.03 | H$_1$ | 0.10 | | | | | 0.3 | |
| 15 | F$_1$ | 0.05 | G$_2$ | 0.03 | H$_1$ | 0.10 | | | | | 0.3 | |
| 16 | F$_1$ | 0.05 | G$_3$ | 0.03 | H$_1$ | 0.10 | | | | | 0.3 | |
| 17 | F$_1$ | 0.05 | G$_1$ | 0.03 | H$_2$ | 0.10 | | | | | 0.3 | |
| 18 | F$_1$ | 0.05 | G$_1$ | 0.03 | H$_3$ | 0.10 | | | | | 0.3 | |
| 19 | F$_1$ | 0.05 | G$_1$ | 0.03 | H$_1$ | 0.10 | | | | 0.3 | | |
| *20 | F$_1$ | 0.05 | G$_1$ | 0.03 | H$_1$ | 0.10 | | | | | | |
| *21 | F$_1$ | 0.05 | G$_1$ | 0.03 | H$_1$ | 0.10 | | | | | | |
| *22 | F$_1$ | 0.05 | G$_1$ | 0.03 | H$_1$ | 0.10 | | | | | | |
| *23 | F$_1$ | 0.05 | G$_1$ | 0.03 | H$_1$ | 0.10 | | | | | | |
| 24 | F$_1$ | 0.05 | G$_1$ | 0.05 | H$_1$ | 0.10 | | | | | 0.3 | |
| *25 | F$_1$ | 0.05 | G$_1$ | 0.03 | H$_1$ | 0.10 | | | | | | |
| *26 | F$_1$ | 0.05 | G$_1$ | 0.03 | H$_1$ | 0.10 | | | | | 0.3 | |
| *27 | F$_1$ | 0.05 | G$_1$ | 0.03 | H$_1$ | 0.10 | | | | | | |

| Run No. | Dibasic Acid Ester (parts by weight) | | Sheet (1 mm in thickness) | | | Tip Portion of 10-ml Syringe 5 Mrad × 60° C. × 30 days |
|---|---|---|---|---|---|---|
| | | | just after irradiation at 5 Mrad | 5 Mrad × 60° C. × 30 days | | |
| | Aromatic | Aliphatic | YI | ΔYI | Bending Cracking (down stroke, mm) | 300 g weight falling break height (cm) |
| 1 | | | 16 | 4 | not cracked | 14 |
| 2 | | | 16 | 4 | " | 15 |
| 3 | | | 17 | 5 | " | 13 |
| 4 | | | 12 | 3 | " | 15 |
| 5 | | | 12 | 3 | " | 16 |
| 6 | | | 10 | 3 | " | 18 |
| 7 | | | 12 | 3 | " | 15 |
| 8 | | | 12 | 3 | " | 16 |

TABLE 1-continued

| | | | | | | | |
|---|---|---|---|---|---|---|---|
| 9 | | | 13 | 3 | " | | 10 |
| 10 | | | 16 | 4 | " | | 11 |
| 11 | | | 11 | 3 | " | | 7 |
| 12 | D₁ 2.0 | | 8 | 2 | " | | 12 |
| 13 | | E₁ 2.0 | 8 | 2 | " | | 12 |
| 14 | | E₂ 2.0 | 8 | 2 | " | | 13 |
| 15 | | E₂ 2.0 | 8 | 2 | " | | 13 |
| 16 | | E₂ 2.0 | 8 | 2 | " | | 13 |
| 17 | | E₂ 2.0 | 8 | 2 | " | | 12 |
| 18 | | E₂ 2.0 | 8 | 2 | " | | 12 |
| 19 | D₁ 2.0 | | 10 | 2 | " | | 13 |
| *20 | | | 5 | 2 | cracked (2) | | 1 |
| *21 | D₁ 2.0 | | 5 | 2 | cracked (3) | | 3 |
| *22 | | E₁ 2.0 | 5 | 2 | cracked (3) | | 3 |
| *23 | | E₁ 2.0 | 5 | 2 | cracked (3) | | 3 |
| 24 | D₁ 2.0 | | 6 | 2 | not cracked | | 8 |
| *25 | | | 5 | 2 | cracked (2) | | 1 |
| *26 | D₁ 2.0 | | 4 | 2 | cracked (3) | | 3 |
| *27 | | | 3 | 1 | cracked (1) | | >1 |

Note
*comparison. **A/B₂ mixing ratio = 50/50

What is claimed is:

1. A polypropylene composition comprising (a) 100 parts by weight of a propylene copolymer, (b) 0.01 to 0.5 parts by weight of a heat stabilizer and (c) 0.1 to 10 parts by weight of a diphenyl ether compound represented by the following general formula:

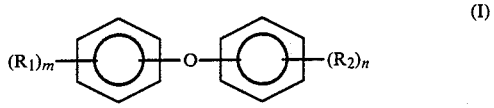

wherein R₁ stands for an alkyl group having 10 to 30 carbon atoms, R₂ stands for an alkyl group having 10 to 30 carbon atoms, and m and n stands for an integer of 0 or 1, with the proviso that the case where each of m and n is 0 is excluded.

2. A polypropylene composition comprising (a) 100 parts by weight of a propylene copolymer, (b) 0.01 to 0.5 parts by weight of a heat stabilizer and (c) 0.1 to 10 parts by weight of a diphenyl ether compound represented by the following general formula:

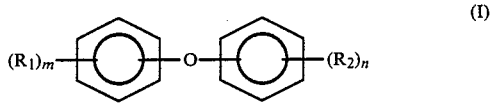

wherein R₁ stands for an alkyl group having 10 to 30 carbon atoms, R₂ stands for an alkyl group having 10 to 30 carbon atoms, and m and n stand for an integer of 0 or 1, with the proviso that the case where each of m and n is 0 is excluded,
and (d) 0.5 to 10 parts by weight of an ester of an aromatic dibasic acid having 8 to 12 carbon atoms or an aliphatic dibasic acid having 4 to 10 carbon atoms with an alkyl group having 1 to 18 carbon atoms.

3. A polypropylene composition as set forth in claim 1, wherein the polypropylene copolymer is a propylene/ethylene copolymer or propylene/butene copolymer containing 0.5 to 5% by weight of ethylene or butene.

4. A polypropylene composition as set forth in claim 1, wherein the heat stabilizer is at least one member selected from the group consisting of triaryl phosphite stabilizers, pentaerythritol phosphite stabilizers, isocyanurate group-containing phenol stabilizers and hindered amine stabilizers.

5. A polypropylene composition as set forth in claim 2, wherein the polypropylene copolymer is a propylene/ethylene copolymer of ethylene/butene copolymer containing 0.5 to 5% by weight of ethylene or butene.

6. A polypropylene composition as set forth in claim 2, wherein the heat stabilizer is at least one member selected from the group consisting of triaryl phosphite stabilizers, pentaerythritol phosphite stabilizers, isocyanurate group-containing phenol stabilizers and hindered amine stabilizers.

7. A polypropylene composition as set forth in claim 2, wherein the dibasic acid ester is a dialkyl adipate, a dialkyl sebacate or a dialkyl phthalate.

8. A polypropylene composition as set forth in claim 2 wherein the diphenyl ether compound of the formula (I) is selected from the group consisting of

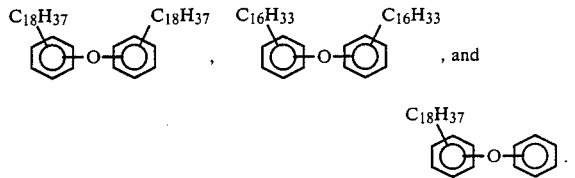

9. A polypropylene composition as set forth in claim 8 wherein the diphenyl ether compound is m-(m-phenoxyphenoxy)diphenyl or a mixture of a monoalkyl diphenyl ether wherein the alkyl group has 18 carbon atoms with a dialkyl diphenyl ether wherein the alkyl groups have 16 carbon atoms.

10. A polypropylene composition as set forth in claim 1 wherein the diphenyl ether compound of the formula (I) is selected from the group consisting of

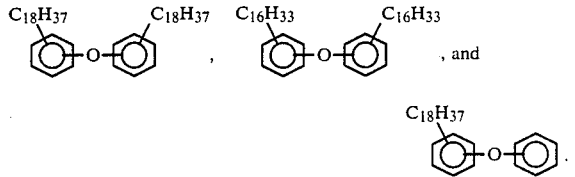

11. A polypropylene composition as set forth in claim 10 wherein the diphenyl ether compound is m-(m-phenoxyphenoxy)diphenyl or a mixture of a monoalkyl diphenyl ether wherein the alkyl group has 18 carbon atoms with a dialkyl diphenyl ether wherein the alkyl groups have 16 carbon atoms.

12. A polypropylene composition as set forth in claim 1 wherein the heat stabilizer is a triaryl phosphite or pentaerythritol phosphite stabilizer.

13. A polypropylene composition as set forth in claim 12 wherein the heat stabilizer is tris(2,4-ditert-butylphenyl)phosphite or distearyl pentaerythritol diphosphite.

14. A polypropylene composition as set forth in claim 1 wherein the heat stabilizer is an isocyanurate group-containing phenol stabilizer selected from the group consisting of tris(3,5-di-ter-butyl-4-hydroxyphenyl)isocyanurate, 1,3,5-tris(4-tert-butyl-3-hydroxy-2,6-dimetnylbenzyl)isocyanurate and 1,3,5-tris(β-(3,5-di-tert-butyl-4-hydroxyphenyl)propionyloxyethyl)isocyanurate.

15. A polypropylene composition as set forth in claim 1 wherein the heat stabilizer is a hindered amine stabilizer selected from the group consisting of dimethyl succinate-1-(2-hydroxyethyl)-4-hydroxy-2,2,6,6-tetramethylpiperazine polycondensate, 4-benzyloxy-2,2,6,6-tetramethylpiperidine, poly(6-(1,1,3,3-tetramethylbutyl)imino-1,3,5-triazin-2,4-diyl)((2,2,6,6-tetramethyl-4-piperidyl)imino)hexamethylene((2,2,6,6-tetramethyl-4-piperidyl)imino), bis(2,2,6,6-tetramethyl-4-methylpiperidine)sebacate, di-(1,2,2,6,6-pentamethyl-4-piperidyl)-2-n-butyl-2-(3,5-di-tert-butyl-4-hydroxybenzyl)malonate and bis(2,2,6,6-tetramethyl-4-carbonyloxypiperidino)-p-dimethylbenzyl.

16. A polypropylene composition as set forth in claim 2 wherein the heat stabilizer is a triaryl phosphite or pentaerythritol phosphite stabilizer.

17. A polypropylene composition as set forth in claim 16 wherein the heat stabilizer is tris(2,4-ditert-butylphenyl)phosphite or distearyl pentaerythritol diphosphite.

18. A polypropylene composition as set forth in claim 2 wherein the heat stabilizer is an isocyanurate group-containing phenol stabilizer selected from the group consisting of tris(3,5-di-ter-butyl-4-hydroxyphenyl)isocyanurate, 1,3,5-tris(4-tert-butyl-3-hydroxy-2,6-dimetnylbenzyl)isocyanurate and 1,3,5-tris(β-(3,5-di-tert-butyl-4-hydroxyphenyl)propionyloxyethyl)isocyanurate.

19. A polypropylene composition as set forth in claim 2 wherein the heat stabilizer is a hindered amine stabilizer selected from the group consisting of dimethyl succinate-1-(2-hydroxyethyl)-4-hydroxy-2,2,6,6-tetramethylpiperazine polycondensate, 4-benzyloxy-2,2,6,6-tetramethylpiperidine, poly(6-(1,1,3,3-tetramethylbutyl)imino-1,3,5-triazin-2,4-diyl)((2,2,6,6-tetramethyl-4-piperidyl)imino)hexamethylene((2,2,6,6-tetramethyl-4-piperdyl)imino), bis(2,2,6,6-tetramethyl-4-methylpiperidine)sebacate, di-(1,2,2,6,6-pentamethyl-4-piperidyl)-2-n-butyl-2-(3,5-di-tert-butyl-4-hydroxybenzyl)malonate and bis(2,2,6,6-tetramethyl-4-carbonyloxypiperidino)-p-dimethylbenzyl.

20. A polypropylene composition as set forth in claim 1 comprising (a) 100 parts by weight of the propylene copolymer, (b) 0.05 to 0.3 parts by weight of the heat stabilizer and (c) 0.2 to 5 parts by weight of the diphenyl ether compound of the general formula (I).

21. A polypropylene composition as set forth in claim 2 comprising (a) 100 parts by weight of the propylene copolymer, (b) 0.05 to 0.3 part by weight of the heat stabilizer, (c) 0.2 to 5 parts by weight of the diphenyl ether compound of the general formula (I), and (d) 1 to 5 parts by weight of said ester of the aromatic or aliphatic dibasic acid.

22. A polypropylene composition as set forth in claim 7 wherein the dibasic acid ester is dibutyl phthalate, diheptyl phthalate, diethylhexyl phthalate, diisononyl phthalate, dioctyl phthalate, dioctyldecyl phthalate, dibutyl adipate, di-n-hexyl adipate, diethylhexyl adipate, dibutyl sebacate and ethylhexyl sebacate.

* * * * *